United States Patent [19]
Arai et al.

[11] Patent Number: 4,781,890

[45] Date of Patent: Nov. 1, 1988

[54] MULTILAYER CHEMICAL ANALYTICAL ELEMENT

[75] Inventors: Fuminori Arai; Kenichiro Yazawa; Harumi Katsuyama, all of Asaka, Japan

[73] Assignee: Fuji Photo Film Co., Ltd., Tokyo, Japan

[21] Appl. No.: 11,386

[22] Filed: Feb. 5, 1987

Related U.S. Application Data

[63] Continuation of Ser. No. 851,286, Apr. 10, 1986, abandoned, which is a continuation of Ser. No. 672,804, Nov. 19, 1984, abandoned.

[30] Foreign Application Priority Data

Nov. 18, 1983 [JP] Japan ................................. 58-217428

[51] Int. Cl.$^4$ .................... G01N 31/22; C12Q 1/54
[52] U.S. Cl. ............................. 422/56; 422/57; 422/58; 436/95; 436/170; 436/175; 435/14; 435/29; 435/805

[58] Field of Search ............... 422/56, 57, 58; 436/95, 436/170, 175; 435/14, 29, 805

[56] References Cited

U.S. PATENT DOCUMENTS

| | | | |
|---|---|---|---|
| 3,992,158 | 11/1976 | Przybylowicz et al. | 422/57 |
| 4,098,574 | 7/1978 | Dappen | 435/14 |
| 4,255,384 | 3/1981 | Kitajima et al. | 422/56 X |

*Primary Examiner*—Barry S. Richman
*Assistant Examiner*—Jill Johnston
*Attorney, Agent, or Firm*—Jules E. Goldberg

[57] ABSTRACT

A multilayer chemical analytical element is employable in quantitative analysis of analyte in a biological fluid such as blood. The element consists of a porous spreading layer, a light-blocking layer and a reagent layer on a water-impermeable light-transmissive support in order. The light-blocking layer contains a titanium dioxide fine powder with no provision of aluminum oxide compound or silicon oxide.

6 Claims, No Drawings

MULTILAYER CHEMICAL ANALYTICAL ELEMENT

This is a continuation of application Ser. No. 851,286, filed Apr. 10, 1986, now abandoned which is a continuation of Ser. No. 672,804, Nov. 19, 1984, now abandoned.

BACKGROUND OF THE INVENTION

1. Field of the Invention

The present invention relates to a multilayer chemical analytical element employable for analysis of a biological fluid. More particularly, the invention relates to a multilayer chemical analytical element free from interference (disturbance) with quantitative analysis of analyte contained in a blood sample (i.e., whole blood, plasma or serum) which is caused by a fluoride contained in the blood sample as preservative.

2. Description of Prior Arts

It is widely employed that a fluoride such as sodium fluoride or lithium fluoride is incorporated into a blood sample (the blood sample means to include whole blood, plasma, and serum, unless otherwise specified in the specification) as a preservative. Since the fluoride serves for preventing glycolysis, in addition to serving as preservative for preventing blood coagulation, the fluoride is appropriately incorporated into a blood sample for measurement of glucose content. See, Handbook of Clinical Tests, 29th revision, originally written by Izumi Kanai, and edited by Masamitsu Kanai (Kanahara Shuppan, Japan, 1983) page 228; and R. D. Henry, D. C. Cannon, J. W. Winkelman, Clinical Chemistry Principles and Technics, 2nd edition (Harper & Row. Publishers, 1974), pages 385–388, etc.

The fluoride (preservative) is incorporated into a blood sample generally by adding the fluoride to the blood just after collection the blood, or collecting a blood into a blood-collecting tube having a fluoride on the inner surface thereof. The fluoride is generally incorporated into a blood sample in an amount of approx. 1 mg. to approx. 10 mg. per 1 ml. in the case that the fluoride is NaF. It has been found that the flourine anion brings about interference effect (disturbance effect) on an analyte to give a lower value (minus error) in analyses using anzymes, particularly an oxidase (e.g., glucose oxidase, cholesterol oxidase, etc.) which are very widely employed at present. Particularly, in the case of analysis of a blood sample containing a great amount of a fluoride as well as in the case of analysis of a blood sample containing a fluoride using a multilayer analytical element through the so-called dry analysis, the minus error caused by the presence of a fluoride anion increases. Therefore, the minus error mentioned above should be solved in the art.

Japanese Patent Publication No. 57(1982)-28277 describes that the minus error observed in the use of an integral multilayer analytical element for quantitative determination of glucose can be avoided by incorporating a pH-adjusting buffer or an organic acid capable of maintaining the surrounding conditions at pH 5.0–5.6 during development of the analysis such as 3,3-dimethylglutaric acid, succinic acid or malic acid into a reagent layer containing a composition for measurement of glucose which comprises glucose oxidase, peroxidase, 4-aminoantipyrine and 7-hydroxy-1-naphthol.

Japanese Patent Application No. 57(1982)-131750 (EP No. 101 945 A1, published on Mar. 7, 1984) describes that the minus error caused by the presence of a fluoride in the use of a multilayer analytical element can be avoided by employing calcium acetate or the like containing calcium cation capable of forming a sparingly water soluble salt with the fluorine anion in conjunction with the composition for glucose or cholresterol analysis which comprises an oxidase such as glucose oxidase or cholesterol oxidase, peroxidase, 4-aminoantipyrine and 1,7-dihydroxynaphthalene.

It has been now discovered by the present inventors that the incorporation of light-blocking layer or light-reflecting layer utilizing the conventionally employed titanium dioxide fine powder provided on the surface with aluminum oxide, silicon oxide, there analogues or a combination thereof into a multilayer analytical element for quantitative measurement of glucose employing the abovedescribed improved technology is still apt to give a minus error in the presence of a fluoride. Moreover, it has been discovered that the multilayer analytical element for quantitative measurement of glucose employing the calcium acetate gives a plus error in the presence of a small amount of a fluoride, while the element gives a minus error in the presence of a large amount of a fluoride. Thus, in the latter case, the fluoride brings about complicated interference effect (disturbance effect) in the analytical element.

SUMMARY OF THE INVENTION

An object of the present invention is to improve analytical accuracy in the use of a multilayer chemical analytical element comprising single or plural reagent layers containing an oxidase, a peroxidase, a hydrogen donor (chromogen), and a coupler (otherwise, a hydrogen donor in the form of a single compound capable of showing color formation or color change upon oxidation can be used in place of the combination of the hydrogen donor and coupler), a light-blocking layer (or light-reflecting layer), and a porous spreading layer which likely suffers minus error or plus error appearing as a result of the interference (disturbance) by a fluoride in a blood sample.

The present invention accomplishes the object by maintaining the pH value in the reagent layer and other layer(s) of the multilayer chemical analytical element at a predetermined range.

The present invention provides a multilayer chemical analytical element comprising a porous spreading layer, a light-blocking layer (including light-reflecting layer) and a reagent layer on a water-impermeable light-transmissive support in order, which is characterized in that said light-blocking layer contains a titanium dioxide fine powder with no provision of aluminum oxide compound or silicon oxide.

DETAILED DESCRIPTION OF THE INVENTION

As the water-permeable light-transmissive support of the invention, there may be used any of supports for the multilayer analytical elements described in Japanese Patent Publication No. 53(1978)-21677 (U.S. Pat. No. 3,992,158), Japanese Patent Provisional Publication No. 55(1980)-164356 (U.S. Pat. No. 4,292,272), etc. Examples of such supports include transparent films or sheets of approx. 50 $\mu$m to 1 mm thick, preferably approx. 80 $\mu$m to 400 $\mu$m thick made of poor hydrophilic or hydrophobic polymers such as cellulose acetate, cellulose acetate butyrate, polyethylene terephthalate, bisphenol A polycarbonate, polystyrene, polymethyl methacrylate, etc. and transparent glass plate of approx. 100 $\mu$m to 2 mm thick, preferably approx. 150 μm to 1 mm thick. If desired, the surface of the support may be subjected to physical or chemical treatment such as ultraviolet light irradiation, corona discharge treatment or the like to enforce its adhesion to the reagent layer, etc. Alternatively, in order to enhance the adhesion between the reagent layer, etc., and the support, a hydrophilic polymer subbing layer composed of a gelatin or the like may be provided on the surface of the support after (or without) subjecting the surface of the support to the physical or chemical treatment.

The reagent layer means a layer containing peroxidase and a hydrogen peroxide indicator showing detectable change in the presence of peroxidase and hydrogen peroxide, and oxidase dispersed or dissolved in a polymer binder having a hydrophilic film-forming property. As described hereinafter, an oxidase layer may be independently provided, and otherwise the oxidase can be incorporated into both of the reagent layer and the oxidase layer. As the hydrogen peroxide indicator, there can be used a combination of a hydrogen donor (chromogen) and a phenol coupler or a naphthol coupler described in the literature "Annals of Clinical Chemistry", 6, 24–27 (1969), U.S. Pat. No. 3,992,158, Japanese Patent Publications No. 55(1980)-25840, No. 56(1981)-45599, and No. 58(1983)-18628 (U.S. Pat. No. 4,042,335) and Japanese Patent Application No. 57(1982)-165233 (Japanese Patent Provisional Publication No. 59(1984)-54962 and EP No. 0 103 903A), etc., triarylimidazole leuco-dyes described in Japanese Patent Publication No. 57(1982)-5519, Japanese Patent Application No. 58(1983)-68009, etc., and a single compound which is a dye precursor compound capable of generating or changing a color by self-coupling in the presence of peroxidase and hydrogen peroxide described in Japanese Patent Publication No. 56(1981)-45599 and No. 58(1983)-18628, etc.

Preferred examples of the hydrogen peroxide indicators are as follows.

Combination of hydrogen donor (chromogen) and coupler:
  Hydrogen donors: 4-aminoantipyrine homologues and derivatives such as 4-aminoantipyrine, 4-amino-2-methyl-3-phenyl-1-(2,4,6-trichlorophenyl)-3-pyrazolin-5-one, etc.
  Couplers: 1-hydroxynaphthalene derivatives such as 1,7-dihydroxynaphthalene, sodium or potassium 1-hydroxynaphthalene-2-sulfonate, etc.
  Triarylimidazole leuco-dyes: 4,5-bis[4-(dimethylamino)phenyl]-2-(4-hydroxy-3,5-dimethoxyphenyl)imidazole, 4-(dimethylamino)phenyl-2-(4-hydroxy-3,5-dimethoxyphenyl)-5-phenethylimidazole, etc.
  Dye precursor compounds: Dianisidine, 4-methoxy-1-naphthol, etc.

As the peroxidase, there can be used a peroxidase originating from plant and animal (EC 1. 11. 1. 7) described in Japanese Patent Publication No. 56(1981)-45599 and No. 57(1982)-5520 (U.S. Pat. No. 4,211,845), etc. and a peroxidase originating from A microorganism (EC 1. 11. 1. 7) described in Japanese Patent Publication No. 58(1983)-5035, etc. Among them, nonspecific peroxidases originating from plant and microorganism are preferred. Examples of preferred peroxidases are that extracted from radish (optimum pH approx. 7.0), that extracted from horse radish, peroxidase of Cochliobolus miyabeanus (optimum pH 5.0–5.3) and peroxidase of Pellicularia filamentosa (optimum pH 4.7–4.9).

As the oxidase, there can be used any of oxidases capable of catalyzing oxidation of the analyte with oxygen ($O_2$) to form $H_2O_2$. Examples of the oxidase which can be used in the present invention include glucose oxidase (EC 1. 1. 3. 4; the optimum pH is approx. 5.6), cholesterol oxidase (EC 1. 1. 3. 6; the optimum pH is approx. 5.8), uricase (EC 1. 7. 3. 3; the optimum pH is approx. 7.5–8.0), sarcosine oxidase (EC 1. 5. 3. 1; the optimum pH is approx. 7.0–9.0), lactate oxidase, pyruvate oxidase, glutamate oxidase, glycerol oxidase, bilirubin oxidase, etc.

In addition to the above-mentioned oxidases, there can be used oxidases described in Japanese Publication No. 56(1981)-45599, Japanese Patent Provisional Publications No. 53(1978)-24893 (GB No. 1,590,738) and No. 57(1982)-208998 and Japanese Patent Application No. 57(1982)-165233 (Japanese Patent Provisional Publication No. 59(1984)-54962 and EP No. 0 103 903 A2), etc. and a combination of different enzymes including these oxidases. If desired, these oxidases can be used in combination with a cofactor and/or a coenzyme.

As the hydrophilic polymer binder used for the preparation of the reagent layer, there can be used any of known hydrophilic polymers employable as hydrophilic polymer binder for the reagent layers in the multilayer analytical elements described in Japanese Patent Publications No. 53(1978)-21677, No. 56(1981)-45599 and No. 57(1982)-5519, Japanese Patent Provisional Publications No. 55(1980)-164356 and No. 57(1982)-208997, etc. Examples of the hydrophilic polymer include gelatin (such as acid-treated gelatin, deionized gelatin, etc.), gelatin derivatives (such as phthalated gelatin, hydroxymethyl acrylate-grafted gelatin, etc.), pullulan, pullulan derivatives, agarose, polyvinyl alcohol, polyvinyl pyrrolidone, polyacrylamide, etc. Among them, gelatin is preferred.

The dry thickness of the reagent layer is within the range of approx. 5 μm to 60 μm, preferably approx. 10 μm to 30 μm. The peroxidase content of the reagent layer is within the range of approx. 5,000 to 100,000 $U/m^2$, preferably approx. 10,000 to 60,000 $U/m^2$. The oxidase content of the reagent layer depends on the nature of the oxidase but generally is within the range of approx. 1,000 to 100,000 $U/m^2$, preferably approx. 3,000 to 50,000 $U/m^2$. In the case of glucose oxidase, the oxidase content is within the range of approx. 2,000 to 40,000 $U/m^2$, preferably approx. 4,000 to 30,000 $U/m^2$. The amount of the hydrogen peroxide indicator in the reagent layer can be properly determined according to the estimated amount of analyte contained in the aqueous liquid sample.

Examples of embodiments of the present invention are an embodiment which includes a reagent layer containing the hydrogen peroxide indicator and peroxidase and an oxidase layer provided above the reagent layer (on the side opposite to the support via the reagent layer, namely, on the side farther than the reagent layer from the support), and an embodiment which comprises incorporation of the oxidease into any one or more of the undermentioned porous spreading layer, a porous layer having a definite area, an adhesive layer, and a light-blocking layer. The embodiment disclosed in the Japanese Patent Provisional Publication No. 57(1982)-208997 comprising incorporation of the oxidase into a layer above the reagent layer containing the hydrogen peroxide indicator and peroxide (hereinafter this layer is specifically referred to as an indicator layer) is one preferable embodiment of the present invention, because an oxygen in air which is required to perform the catalytic reaction of the substrate by the oxidase is efficiently transferred through diffusion to contact the oxidase, whereby the oxidation reaction catalytically caused by the oxidase proceeds smoothly and rapidly to bring about highly efficient color formation and shortening of the analytical period. The amount of the oxidase incorporated into a layer above the reagent layer may be the same as the amount described hereinbefore. The oxidase layer can be provided to the indicator layer directly or via the under-mentioned intermediate layer.

A pH buffer may be incorporated in the indicator layer in order to keep the layer at the optimum pH value for the oxidase or peroxidase or in the vicinity thereof, or to keep the layer within a pH range in which the dye-forming (or color-changing) reaction of the hydrogen peroxide indicator rapidly proceeds without substantial interference by the activity of both enzyme, that is, to keep the reagent layer under analytical conditions at a pH value within approx. 4.0 to 7.5, preferably approx. 4.5 to 7.0. In the case that the oxidase layer is provided above the reagent layer or the oxidase is incorporated into any layer above the reagent layer, a buffer reagent capable of assuring the optimum pH value for the oxidase or a value in the vicinity thereof can be incorporated into the oxidase layer or oxidase-containing layer and a pH buffer reagent capable of assuring the optimum pH value for the peroxidase or a value in the vicinity thereof, otherwise at least assuring a pH value at which the activity of the peroxidase is substantially not disturbed and the color forming (or color changing) reaction of the hydrogen peroxide indicator proceeds smoothly and rapidly. As the pH buffer, there can be used any of known pH buffers described in the following literatures: "Biochemistry", 5 (2), 467–477 (1966); R. M. C. Dawson et al. "Data for Biochemical Research" the second edition (Oxford at the Clarendon Press, 1969) pp. 476–508; "Analytical Biochemistry", 104, 300–310 (1980); "Kagaku Binran Kisohen" pp 1312–1320, edited by the Japan Chemical Society (Maruzen, Tokyo, 1966); "Biochemistry Data Book I" pp. 17–24 edited by the Japan Biochemical Society (Tokyo Kagaku Dojin Ltd., 1979); Japanese Patent Publication No. 57 (1982)-28277 (U.S. Pat. No. 4,098,574), etc.

The oxygen-permeable protein-impermeable light-blocking layer (hereinafter often referred to simply as light-blocking layer) is provided on the reagent layer (or oxidase layer). The term "oxygen-permeable protein-impermeable" used herein means that oxygen ($O_2$) in air can substantially permeate through the layer, but proteins substantially do not permeate through the layer, when water serving as a solvent of the aqueous liquid sample penetrates into this layer to wet or swell this layer under analytical conditions. The term "protein" used herein refers to a common protein having a molecular weight of approx. 5,000 or higher, particularly a conjugated protein having hydrogen peroxide-decomposition activity such as catalase (having a molecular weight of approx. 250,000) and hemeprotein, typically hemoglobin (having a molecular weight of approx. 65,000). The oxygen-permeable protein-impermeable light-blocking layer is usually a nonporous layer which comprises a small amount of a light-blocking or light-reflecting titanium dioxide fine powder dispersed in a small amount of a hydrophilic (or weak hydrophilic) polymer binder having film-forming property. In the measurement of the color generated or changed in the reagent layer by reflection photometry from the side of the transparent (light-transmissive) support, the light-blocking layer blocks the color of the aqueous liquid sample spotted on the spreading layer mentioned later, particularly red color originating from hemoglobin in the case that whole blood is used. Moreover, the light-blocking layer functions as a light-reflecting layer as well as a background layer.

Examples of the titanium dioxide fine powder to be incorporated in the light-blocking layer include titanium dioxide fine powders provided (mainly coated) on the surface with no such compounds as aluminum compounds containing trivalent aluminum and oxygen, for instance, aluminum oxide (alumina, $Al_2O_3$), water-containing aluminum oxide (e.g., $Al_2O_3.H_2O$, $Al_2O_3.3H_2O$, etc), and compound containing trivalent aluminum, other element(s) (e.g., tetravalent silicon) and oxygen (in the specification, these aluminum oxides and its analogues are termed by aluminum oxide compound), and silicon oxide (silica, $SiO_4$).

The titanium dioxide fine powder may be in any crystal forms such as anatase, rutile, and brookite. The titanium dioxide fine powder generally has an average size ranging from approx. 0.1 $\mu$m to 1.0 $\mu$m (a titanium dioxide having such size is commercially available) and preferably an average size ranging from approx. 0.15 $\mu$m to 0.5 $\mu$m. Examples of the titanium dioxide fine powder with provision of neither aluminum oxide compound nor silicon oxide include titanium dioxide fine powder with no treatment and titanium dioxide fine powder treated on the surface with titanium hydroxide. The former aluminum dioxide fine power with no treatment is preferred.

Examples of the hydrophilic (or weak hydrophilic) polymer binders having film-forming property include gelatin (such as acid-treated gelatin, deionized gelatin, etc.), gelatin derivatives (such as phthalated gelatin, hydroxymethyl acrylate-grafted gelatin, etc.), polyvinyl alcohol, regenerated cellulose, cellulose acetate (such as cellulose diacetate), etc. Among them, gelatin and gelatin derivatives are preferable. Gelatin and gelatin derivatives can be used together with a conventional hardener (i.e., cross-linking agent). When these polymers are used for the preparation of an adhesive layer mentioned later, various hydrophilic polymers can be used as the polymer binders for the light-blocking layer like the reagent layer.

The ratio of the light-blocking fine powder to the polymer binder (dry basis) in the light-blocking layer can vary, provided that the produced light-blocking layer is so non-porous that the layer can allow permeation of oxygen but does not allow permeation of protein (the term "non-porous" includes such a microporous structure that the size of the pore or void is smaller than the average size with which the spreading effect or metering effect occurs in the porous spreading layer occurs). Specifically, the ratio of the light-blocking fine powder to the polymer binder (dry basis) can be within the range of approx. 10:0.6 to 10:1.8, preferably approx. 10:0.8 to 10:1.5, by weight. The thickness of the light-blocking layer can be within the range of approx. 3 $\mu$m to 30 $\mu$m, preferably approx. 5 $\mu$m to 20 $\mu$m, on the dry basis, If necessary, an intermediate layer can be provided between the reagent layer and the light-blocking layer and also between the reagent layer and the oxidase layer in the case of the oxidase layer is provided. For the preparation of these intermediate layers, hydrophilic polymers having film-forming property similar to those used for the reagent layer can be used. The thickness of the intermediate layer can be within the range of approx.

0.2 μm to 10 μm, preferably approx. 0.5 μm to 7 μm.

If necessary, an adhesive layer can be provided between the light-blocking layer and the porous spreading layer (described later). For the preparation of the adhesive layer, there can be used hydrophilic polymers which have film-forming property similar to those used for the reagent layer and which can bond the porous spreading layer and the light-blocking layer to form an integrated structure when the adhesive layer is wetted or swollen with water. The thickness of the adhesive layer can be within the range of approx. 0.5 μm to 20 μm, preferably approx. 1 μm to 10 μm. Preferred hydrophilic polymers employable for the preparation of the intermediate layer and the adhesive layer include gelatin, gelatin derivatives, polyacrylamide, and polyvinyl alcohol.

If necessary, a surfactant can be incorporated into the reagent layer, the light-blocking layer, the intermediate layer, the adhesive layer, the oxidase layer (if provided), and the indicator layer. As the surfactant, a nonionic surfactant, particularly a nonionic surfactant containing 8 to 15 oxyethylene or oxypropylene units in the linear chain structure is preferred. If desired, known additives such as a hardener (cross-linking agent), a softening agent, a plasticizer, etc. can be further incorporated into these layers.

On the light-blocking layer, the porous spreading layer or a porous layer (patch) having a definite surface area is provided directly or through an adhesive layer. As the porous spreading layer, there can be adopted a non-fibrous isotropic porous medium layer described in Japanese Patent Publication No. 53(1978)-21677 (U.S. Pat. No. 3,992,158), Japanese Patent Provisional Publications No. 55(1980)-90859 (U.S. Pat. No. 4,258,001) and No. 58(1983)-123458, etc.; a fabric spreading layer described in Japanese Patent Provisional Publications No. 55(1980)-164356 and No. 57(1982)-66359, etc.; and a layer composed of a paper sheet containing a polyolefin polymer filament pulp described in Japanese Patent Provisional Publication No. 57(1982)-148250. As the porous layer having a definite surface, there can be adopted a porous material described in Japanese Utility Model Provisional Publication No. 57(1982)-42951 (DE No. 31 33 538A), etc. Among them, the spreading layer is preferred. Among various spreading layers, more preferred are a membrane filter layer (i.e., blushed polymer layer), a three-dimensional lattice-particulate structure layer formed by bonding polymer beads to one another under point contact with a polymer adhesive which is not swollen with water, and the fabric spreading layer. The spreading layer and the porous layer having a definite surface can be provided according to the methods described in the aforementioned patent specifications.

A surfactant, preferably the aforementioned nonionic surfactant, can be incorporated into the porous spreading layer (hereinafter often referred to simply as spreading layer), if necessary. Further, part of a reagent containing an enzyme such as cholesterol esterase can be incorporated into the porous spreading layer as described in Japanese Patent Publication No. 55(1980)-45599. The light-blocking fine powder can be also incorporated into the porous spreading layer.

The multilayer analytical element of the invention can contain a compound containing a cation capable of forming with a fluorine anion a salt sparingly soluble in water (hereinafter referred to as a sparingly soluble fluoride salt) in the reagent layer or any other layer(s) (including the porous spreading layer or a porous layer having a definite surface area) located above the reagent layer. The above-mentioned compound is hereinafter referred to as a sparingly soluble fluoride salt-forming compound. The term "a salt sparingly soluble in water" means a salt having a solubility in 100 g. of water at 25° C. of not higher than 0.2 g. As the sparingly soluble fluoride salt-forming compound can be any one of the sparingly soluble fluoride salt-forming compounds disclosed in the aforementioned Japanese Patent Application No. 57(1982)-131750.

As the cation contained in the sparingly soluble fluoride salt-forming compound, there can be mentioned $Ca^{2+}$ and $Mg^{2+}$ which further serves for stabilizing the enzymes such as a oxidase and peroxidase. Preferable examples of the counter anion include a lower aliphatic monocarboxylic acid anion, a lower aliphatic dicarboxylic acid anion, a hydroxycarboxylic acid anion, a halogen anion, and a phosphoric acid anion. The sparingly soluble fluoride salt-forming compound can be incorporated into at least one of the constituting layers, namely, a porous spreading layer, a porous layer having a definite surface area, an adhesive layer, a light-blocking layer, a reagent layer, an oxidase layer (if provided), and intermediate layers. Preferably, the sparingly soluble fluoride salt-forming compound is incorporated into one or plural layers selected from the group consisting of the adhesive layer, light-blocking layer and oxidase layer. The sparingly soluble fluoride salt-forming compound is generally incorporated into the multilayer analytical element in an amount of 0.1 meq. to 1 eq. per 1 $m^2$ of the element. The sparingly soluble fluoride salt-forming compound can be incorporated into the multilayer chemical analytical element by dissolving or dispersing the compound in a coating solution for the preparation of the desired layer and forming the coated layer or by dissolving the compound in a wetting water to be supplied to an adhesive layer and superposing thereon a porous spreading layer.

The multilayer chemical analytical element of the invention containing the sparingly soluble fluoride salt-forming compound is particularly preferred because the interference (disturbance) caused by a fluoride in a blood sample is obviated regardless of the content of the fluoride in the blood sample (in the range of 0–approx. 15 mg./ml as NaF) to give such a measured value indicating content of the analyte corresponding to that obtained in a blood sample containing no fluoride.

The multilayer chemical analytical element which is prepared by integrating the above-mentioned layers can be cut into an appropriate size and encased in a slide frame (e.g., one disclosed in Japanese Patent Provisional Publications No. 54(1979)-156079 and No. 57(1984)-63452; Japanese Utility Model Provisional Publications No. 56(1981)-142454 and No. 58(1983)-32350; and Japanese Patent Disclosure (Tokuhyo) No. 58(1983)-501144) to give an analytical slide. The multilayer analytical element can be employed in the form of a longitudinal tape or strip fixed to or encased in an aperture card, etc.

The above description has been made with reference to an integral multilayer analytical element in which all layers are united in one structure. However, the multilayer chemical analytical element of the present invention is not limited to the integral element, and can be prepared in the form of a separate-type multilayer analytical element in which certain layer or layers are separated from each other.

The multilayer analytical element of the invention can be utilized to analyze quantitatively an analyte in an aqueous liquid sample mainly through colorimetry according to the methods described in the aforementioned patent publications, Clinical Chemistry, 24(8), 1335–1342 (1979), etc.

Since the multilayer chemical analytical element contains an enzyme, the analysis can be performed by the end point process comprising colorimetric determination after incubation at 30°–40° C. for 3–30 min., and preferably for 4–15 min., or by the rate process utilizing the same incubation temperature and comprising two or more colorimetric measurements at a constant interval after lapse of the reaction inducing period.

The present invention is further described by the following examples.

REFERENCE EXAMPLE 1

In 40 ml. of water was dispersed 5 g. of (A) a titanium dioxide fine powder treated on the surface with $Al_2O_3$, (B) a titanium dioxide fine powder treated on the surface with a mixed oxide $Al_2O_3.SiO_2$, or (C) a titanium dioxide fine powder with no treatment on the surface. To the resulting dispersion was added 1 g. of NaF, and the mixture was agitated with a stirrer having a polytetrafluoroethylene. The dispersion was then allowed to stand for 1 hour, and its pH value was measured. The results are set forth in Table 1. The comparison experiment was performed using the same solution which contained no titanium dioxide fine powder.

TABLE 1

| | $TiO_2$ type (particle size) | | | |
|---|---|---|---|---|
| | Anatase (0.15–0.25 μm) | | Rutile (0.20–0.35 μm) | No Addition (blank) |
| Surface Treatment | A | C | A | B | — |
| pH Value | 11.5 | 8.4 | 11.7 | 11.3 | 8.0 |

It is apparent from the results set forth in Table 1 that the pH value of a dispersion containing a titanium dioxide fine powder treated on the surface with $Al_2O_3$ or $Al_2O_3.SiO_2$ increases extremely, while the pH value of a dispersion containing a titanium dioxide fine powder with no surface treatment is at a similar level to the value given in the blank run.

REFERENCE EXAMPLE 2

Ten weight parts of a titanium dioxide fine powder (anatase type, particle size: 0.15–0.25 μm) treated on the surface with $Al_2O_3$ (alumina) or a titanium dioxide fine powder (anatase type, particle size: 0.15–0.25 μm) with no surface treatment, 1 weight part of gelatin, and 20 weight parts of water were mixed and dispersed to give a dispersion. The resulting dispersion was coated on a polyethylene terephthalate (PET) film and dried to give a dry layer of 5 μm thick. Thus, two titanium dioxide/gelatin coating film sets were prepared.

On each coating layer were spotted 10 μl. of NaF-containing containing water and NaF-free water (blank) independently so that the spotted solutions were absorbed by the coating layer. Just after allowing to stand it at 25° C. for 5 min. in a sealed box, the pH value on the surface of the coating layer under wetting conditions was measured by means of a surface pH measurement electrodes (GS-165F, Toa Denpa Kogyo Co., Ltd., Japan) under pressure. The results are set forth in Table 2.

TABLE 2

(Surface pH Value of Wetted Coating Layer)

| | NaF content in water (mg/ml water) | | | | |
|---|---|---|---|---|---|
| | 0 (blank) | 5 | 10 | 15 | 20 |
| $TiO_2$ with alumina treatment | 7.4 | 8.0 | 8.7 | 9.2 | 9.8 |
| $TiO_2$ with no treatment | 7.4 | 7.4 | 7.4 | 7.5 | 7.6 |

It is noted in the alumina-free titanium dioxide fine powder/gelatin coating layer that the increase of NaF content in the NaF-containing solution hardly induced substantial increase of the pH value of the coating layer, and particularly no change of pH value was observed as far as the NaF content was in the ordinarily employed range of 0–10 mg/ml. In contrast, it is noted in the alumina-treated titanium dioxide fine powder/gelatin coating layer that the increase of NaF content induced prominent increase of pH value of the coating layer, and this prominent pH change was clearly observed in the NaF content range of 0–10 mg/ml.

EXAMPLE 1

A transparent polyethylene terephthalate (PET) film having a gelatin subbing layer and a thickness of 180 μm was coated with the reagent layer (dry thickness: approx. 15 μm) for glucose analysis having the following composition, using an aqueous solution and subsequent drying treatment.

| | |
|---|---|
| Peroxidase | 25,000 IU |
| Oxidase | 15,000 IU |
| 1,7-Dihydroxynaphthalene | 5 g. |
| 4-Aminoantipyrine | 5 g. |
| Gelatin | 200 g. |
| Polyoxyethylenenonylphenyl ether | 2 g. |

The surface of the reagent layer for glucose analysis was coated with an oxygen-permeable protein impermeable light-blocking layer (dry thickness: approx. 7 μm) having the following composition, using an aqueous dispersion and subsequent drying treatment.

| | |
|---|---|
| Titanium dioxide fine powder with no surface treatment (anatase type, particle size 0.15–0.25 μm) | 100 g. |
| Gelatin | 10 g. |

On the light-blocking layer was provided an adhesive layer (dry thickness: approx. 2 μm) having the following composition, using an aqueous solution and subsequent drying treatment.

| | |
|---|---|
| Gelatin | 4 g. |
| Polyoxyethylenenonylphenyl ether | 0.1 g. |

Water was then supplied in an amount of approx. 30 g/m² over the whole surface of the adhesive layer to wet the layers, and a 100% cotton broadcloth (100 count twin broadcloth) was superposed thereon under low pressure. The resulting laminated structure was dried to prepare an integral multilayer chemical analytical element employable for quantitative determination of glucose.

COMPARISON EXAMPLE 1

The procedure of Example 1 was repeated except that the titanium dioxide fine powder with no surface treatment was replaced with a titanium dioxide fine powder treated on the surface with $Al_2O_3.SiO_2$ (rutile type, particle size 0.20–0.35 μm). Thus, an integral multilayer chemical analytical element for quantitative determination of glucose was prepared.

10 μl. of human plasma containing different amount of NaF set forth in Table 3 was spotted on the spreading layer of each integral chemical multilayer analytical element and the analytical element was then incubated at 37° C. for 10 minutes. Just upon completion of the incubation, the pH value on the surface of the wetted spreading layer was measured by means of the surface pH value measuring electrode (GS-165F). The results are set forth in Table 3.

TABLE 3

| | NaF content in human plasma (mg/ml plasma) | | | | |
|---|---|---|---|---|---|
| | 0 (blank) | 5 | 10 | 15 | 20 |
| Ex. 1 (Present Invention) | 5.76 | 5.90 | 5.90 | 5.95 | 6.05 |
| Com. Ex. 1 (Comparison) | 5.76 | 6.75 | 7.15 | 7.42 | 7.73 |

It is noted in the multilayer analytical element for the quantitative determination of glucose having a light-blocking layer containing an alumina-free titanium dioxide fine powder of the present invention that the increase of NaF content in the plasma hardly induced substantial increase of the pH value of the spreading layer, and particularly no substantial change of pH value was observed on the spreading layer as far as the NaF content was in such a range of 0–10 mg/ml (plasma) as employed for incorporation into a plasma. In contrast, it is noted in the comparison multilayer analytical element for the quantitative determination of glucose having a light-blocking layer containing a titanium dioxide fine powder treated on the surface with $Al_2O_3.SiO_2$ hat the increase of NaF content in the plasma induced prominent increase of pH value of the spreading layer, and this prominent pH change was clearly observed in the NaF content range of 0–10 mg/ml (plasma).

EXAMPLE 2

The procedure of Example 1 was repeated except that the adhesive layer was prepared using the following composition. Thus, an integral multilayer analytical element for quantitative determination of glucose was obtained.

| Gelatin | 4 g. |
|---|---|
| Calcium acetate | 1.8 g. |
| Polyoxyethylenenonylphenyl ether | 0.1 g. |

COMPARISON EXAMPLE 2

The procedure of Example 1 was repeated except that the adhesive layer was prepared using the composition employed in Example 2 and that the titanium dioxide fine powder with no surface treatment was replaced with a titanium dioxide fine powder treated on the surface with $Al_2O_3.SiO_2$ (rutile type, particle size: 0.20–0.35 μm). Thus, an integral multilayer chemical analytical element for quantitative determination of glucose for comparison was prepared.

The two analytical elements prepared in the examples were cut into square chips (15 mm × 15 mm) and encased in plastic mounts disclosed in Japanese Patent Provisional Publication No. 57(1982)-63452 to give chemical analytical slides for quantitative determination of glucose. These were named a chemical analytical slide of the invention and a chemical analytical slide for comparison.

10 μl. of human plasma containing different amount of NaF set forth in Table 4 was spotted on the spreading layer of each chemical analytical slide and the analytical slide was then incubated at 37° C. for 6 minutes in a sealed container. Upon completion of the incubation, pH value on the surface of the swollen spreading layer was measured by means of the surface pH value measuring electrode (GS-165F). The results are set forth in Table 4.

Independently, 10 μl. of the same human plasma as above was spotted on the spreading layer of each chemical analytical slide and the analytical slide was then incubated at 37° C. for 6 minutes in a chemical analytical apparatus. The incubated slide was subjected to reflection photometry using a visible light (central wavelength: 500 nm) which was applied thereto from PET film side. Subsequently, the glucose content in the plasma was determined by colorimetry. The results are set forth in Table 4.

TABLE 4

| | NaF content in human plasma (mg/ml plasma) | | | |
|---|---|---|---|---|
| | 0 (blank) | 5 | 10 | 15 |
| Chemical Analytical Slide of Invention | | | | |
| pH Value on Spreading Layer | 6.40 | 6.42 | 6.39 | 6.41 |
| Measured Glucose Content (mg/dl) | 101 | 101 | 100 | 99 |
| Chemical Analytical Slide for Comparison | | | | |
| pH Value on Spreading Layer | 6.40 | 6.49 | 7.32 | 7.71 |
| Measured Glucose Content (mg/dl) | 102 | 105 | 109 | 112 |

It is noted that the chemical analytical slide for the quantitative determination of glucose having a light-blocking layer containing an alumina-free titanium dioxide fine powder of the invention gave substantially the same glucose content (measured value) regardless of the concentration of NaF in the plasma. In contrast, it is noted that the chemical analytical slide for comparison having a light-blocking layer containing a titanium dioxide fine powder treated on the surface with $Al_2O_3.SiO_2$ suffered interference (disturbance) caused by NaF in the plasma, and that the interference (disturbance) was prominent at a NaF content of higher than 5 mg/ml (plasma).

EXAMPLE 3

A transparent polyethylene terephthalate (PET) film having a gelatin subbing layer and a thickness of 180 μm was coated with the indicator layer (dry thickness: approx. 15 μm) having the following composition, using an aqueous solution and subsequent drying treatment.

| | |
|---|---|
| Peroxidase | 25,000 IU |
| Oxidase | 15,000 IU |
| 1,7-Dihydroxynaphthalene | 5 g. |
| 4-Aminoantipyrine | 5 g. |
| Gelatin | 200 g. |
| Polyoxyethylenenonylphenyl ether | 2 g. |

On the indicator layer was provided a glucose oxidase layer (dry thickness: approx. 2 μm) having the following composition, using an aqueous solution and subsequent drying treatment.

| | |
|---|---|
| Gelatin | 4.6 g. |
| Glucose oxidase | 4,000 IU |
| 3,3-Dimethylglutaric acid | 0.1 g. |
| Polyoxyethylenenonylphenyl ether | 0.1 g. |

The surface of the glucose oxidase layer was coated with an oxygen-permeable protein-impermeable light-blocking layer (dry thickness: approx. 7 μm) having the following composition, using an aqueous dispersion and subsequent drying treatment.

| | |
|---|---|
| Titanium dioxide fine powder with no surface treatment (anatase type, particle size: 0.15–0.25 μm) | 100 g. |
| Gelatin | 10 g. |

On the light-blocking layer was provided an adhesive layer (dry thickness: approx. 2 μm) having the following composition, using an aqueous solution and subsequent drying treatment.

| | |
|---|---|
| Gelatin | 10 g. |
| Calcium acetate | 5 g. |
| Polyoxyethylenenonylphenyl ether | 0.1 g. |

Water was then supplied in an amount of approx. 30 g/m² over the whole surface of the adhesive layer to wet the layers, and a 100% cotton broadcloth (100 count twin broadcloth) was superposed thereon under low pressure. The resulting laminated structure was dried to prepare an integral multilayer chemical analytical element employable for quantitative determination of glucose.

Thus prepared integral multilayer chemical analytical element for quantitative determination of glucose was employed for measuring glucose content in a human plasma and whole blood having different content of NaF in the same manner as in Example 2. There were determined the correct values of glucose content (measured value) regardless of the concentration of NaF in the plasma or whole blood as in Example 2.

EXAMPLE 4

The procedure of Example 2 or 3 was repeated except that the titanium dioxide fine powder (rutile type, particle size: 0.20–0.35 μm) with no surface treatment was employed. Thus, integral multilayer chemical analytical elements for quantitative determination of glucose were prepared.

Thus prepared integral multilayer chemical analytical element for quantitative analysis of glucose was employed for measuring glucose content in a human plasma having different content of NaF in the same manner as in Example 2. There were determined the correct values of glucose content (measured value) regardless of the concentration of NaF in the plasma in Example 2.

We claim:

1. In a multilayer chemical analytical element which includes a porous spreading layer, a light-blocking layer and a reagent layer on a water-impermeable light-transmissive support in order, wherein the improvement comprises having said light-blocking layer contain a titanium dioxide fine powder having neither an aluminum oxide compound nor silicon oxide, the element containing a compound having a cation which is capable of forming a sparingly water soluble salt with flourine anion.

2. The analytical element according to claim 1, wherein said reagent layer contains peroxidase and a hydrogen peroxide indicator which is capable of showing a detectable change in the presence of said peroxidase and hydrogen peroxide.

3. The analytical element according to claim 1, wherein said cation is a cation selected from the group consisting of divalent calcium and divalent magnesium.

4. The analytical element according to claim 1, wherein said titanium dioxide fine powder is in a crystalline form selected from the group consisting of anatase, rutile and brookite.

5. The analytical element according to claim 1, wherein said light-blocking layer includes a surfactant.

6. The analytical element according to claim 5, wherein said surfactant is a non-ionic surfactant.

* * * * *